(12) United States Patent
Shanks

(10) Patent No.: US 12,125,301 B2
(45) Date of Patent: Oct. 22, 2024

(54) MODULAR SPINAL IMPLANT

(71) Applicant: T. S. Shanks, PLLC, Union City, TN (US)

(72) Inventor: Todd Shanks, Dallas, TX (US)

(73) Assignee: T.S. Shanks, PLLC, Union City, TN (US)

( * ) Notice: Subject to any disclaimer, the term of this patent is extended or adjusted under 35 U.S.C. 154(b) by 285 days.

(21) Appl. No.: 17/571,488

(22) Filed: Jan. 9, 2022

(65) Prior Publication Data

US 2022/0130162 A1  Apr. 28, 2022

Related U.S. Application Data

(63) Continuation of application No. 17/183,420, filed on Feb. 24, 2021, now Pat. No. 11,270,144.

(60) Provisional application No. 63/032,543, filed on May 30, 2020.

(51) Int. Cl.
| | |
|---|---|
| A61F 2/44 | (2006.01) |
| A61F 2/46 | (2006.01) |
| G06V 30/12 | (2022.01) |
| G06V 30/14 | (2022.01) |
| G06V 30/142 | (2022.01) |
| G06V 30/148 | (2022.01) |
| A61F 2/30 | (2006.01) |
| G06V 30/10 | (2022.01) |

(52) U.S. Cl.
CPC .......... *G06V 30/127* (2022.01); *A61F 2/4425* (2013.01); *A61F 2/4611* (2013.01); *G06V 30/133* (2022.01); *G06V 30/142* (2022.01); *G06V 30/1452* (2022.01); *G06V 30/1456* (2022.01); *G06V 30/153* (2022.01); *A61F 2002/30224* (2013.01); *A61F 2002/443* (2013.01); *A61F 2002/4677* (2013.01); *G06V 30/10* (2022.01)

(58) Field of Classification Search
CPC .. A61F 2/442; A61F 2/4425; A61F 2002/443; A61F 2002/448; A61F 2002/4485; A61F 2/4611; A61F 2002/4677
USPC .......................................... 623/17.11–17.16
See application file for complete search history.

(56) References Cited

U.S. PATENT DOCUMENTS

| | | | |
|---|---|---|---|
| 7,708,777 B2 | 5/2010 | O'Neil et al. | |
| 7,909,876 B2 | 3/2011 | Dooris et al. | |
| 9,561,116 B2 | 2/2017 | Weiman et al. | |
| 9,603,717 B2* | 3/2017 | Ibarra | A61F 2/442 |
| 9,962,269 B2* | 5/2018 | Jones | A61F 2/4465 |
| 2003/0187506 A1 | 10/2003 | Ross et al. | |
| 2012/0209384 A1* | 8/2012 | Arnold | A61F 2/28 623/17.15 |
| 2017/0245997 A1* | 8/2017 | Trischler | A61F 2/4657 |

\* cited by examiner

*Primary Examiner* — Eduardo C Robert
*Assistant Examiner* — Christina Negrellirodriguez
(74) *Attorney, Agent, or Firm* — BUSINESS PATENT LAW, PLLC

(57) ABSTRACT

The current modular implant is particularly useful in spinal surgical procedures. The modular implant can be provided with two anchors and a central section.

18 Claims, 8 Drawing Sheets

MODULAR SPINAL IMPLANT

This Application claims priority to application Ser. No. 17/183,420—Modular Spinal Implant—filed Feb. 24, 2021 that claims the benefit of U.S. Provisional Application 63/032,543—Spinal Implant—filed on May 30, 2020.

BACKGROUND OF THE INVENTION

A. Field of the Invention

Among other things, the present invention is particularly suited for implantation into mammalian spinal tissues. The current invention is a modular spinal implant. Preferred embodiments of the spinal implant include a central section connected to first and second endplates. The present invention can also include a spinal implant component and an insertion device component.

B. Description of the Previous Art

Any discussion of references cited herein merely summarizes the disclosures of the cited references. Applicant makes no admission that any cited reference or portion thereof is relevant prior art. Applicant reserves the right to challenge the accuracy, relevancy and veracity of the cited references. Patents and Published Patent Applications may indicate a state-of-art include: 1) U.S. Pat. No. 9,603,717—Ibarra, et al. discloses a system and method for an expandable intervertebral implant; 2) U.S. Pat. No. 8,323,1675—Rhoda discloses an intervertebral implant; 3) U.S. Pat. No. 9,561,116—Weiman, et al. discloses an expandable fusion device and method of installation thereof; 4) U.S. Pat. No. 7,708,777—O'Neil, et al. discloses modular intervertebral disc replacements; 5) U.S. Pat. No. 7,909,876—Dooris, et al. disclose an intervertebral disc prosthesis with shear-limiting core; 6) U.S. Pat. No. 9,962,269—Jones, et al. discloses an implant with independent endplates; and 7) US Published Patent Application 20030187506—Ross, et al. discloses a modular disc prosthesis.

SUMMARY OF THE INVENTION

The present invention provides a biocompatible implant for bone, and the invention is particularly suited for implantation in to spinal tissues.

Advantageously, the current modular spinal implant can be assembled within the surgical field or surgically created cavity or the spinal implant can also be assembled prior to insertion into the surgically created cavity. Unlike prior art spinal implants, the insertion tool's handles and implantable anchors or endplates can also be utilized to impose distraction forces to the surgical field which can improve the ease of surgical placement of the central section between the anchors implanted into the surgically created cavity. Subsequent to the placement of the central section between the endplates, the insertion device's handles can be removed—leaving the present modular spinal implant surgically implanted in the surgically created cavity.

An aspect of the present invention is to provide a spinal implant.

Another aspect of the present invention is to provide a modular spinal implant.

It is still another aspect of the present invention to provide a modular spinal implant that can be assembled in the surgically created cavity.

Yet another aspect of the present invention is to provide a spinal implant system including a spinal implant component and a complementary insertion device component.

Still another aspect of the present invention is to provide a modular spinal implant including a central section connected to first and second endplates secured to the surgically created cavity.

Yet another aspect of the present invention is to provide a spinal implant that can be inserted by anterior or posterior surgical procedures.

Yet still another aspect of the present invention is to provide a spinal system where the combination of the opposed endplates and the handles of the insertion tool component function as a distraction device prior to insertion of the central section of the spinal implant.

Yet another aspect of the present invention is to provide endplates that create lordosis for the implanted modular spinal implant.

Still another aspect of the present invention is to provide a central section with a chamber for receiving graft and other medically useful substances that can be dispersed outward from the central section subsequent to closure of the surgical site.

Yet another aspect of the present invention is to provide a surgical implant that can be implanted into the surgically created cavity with or without radiography.

Yet still another aspect of the present invention is to provide a cover plate that further secures the spinal implant implanted into the surgically created cavity.

A preferred embodiment of the current invention can be described as a modular spinal implant adapted for implantation into a surgically created cavity; the modular spinal implant comprising: a) a first endplate, positioned at a first site of the surgically created cavity, including a first outer perimeter sized to correspond with a first longitudinal side of a central section of the spinal implant; the first endplate comprising: i) a first planar side including a first tongue perpendicular to the first planar side and extending toward the center of the spinal implant, wherein the first tongue is of lesser length than the first planar side; ii) a second side opposed to the first planar side; the second side comprising grippers adapted to engage the first site; iii) opposed first and second curved edges positioned between opposed first and second linear edges; the edges extending between the first planar side and the second side, wherein the first linear edge is of lesser length than the second linear edge creating an angled second side relative to the first planar side; iv) first and second slots traversing an approximate length of each curved edge; b) a second endplate, positioned at a second site of the surgically created cavity, including a second outer perimeter sized to correspond with a second longitudinal side of the central section of the spinal implant; the second endplate comprising: i) a first planar side including a second tongue perpendicular to the first planar side and extending toward the first tongue, wherein the second tongue is of lesser length than the first planar side; ii) a second side opposed to the first planar side; the second side comprising grippers adapted to engage the second site; iii) opposed first and second curved margins positioned between opposed first and second linear margins; the margins extending between the first planar side and the second side, wherein the first margin is of lesser length than the second linear margin creating an angled second side relative to the first planar side; iv) first and second slots traversing an approximate length of each curved margin; and c) the central section connected to the first endplate and the second endplate; the central section comprising: i) a first groove positioned on the first longitudinal side of the central section and extending inward from the first longitudinal side of the central section; the first groove comprising a first gateway, in the first longitudinal side of the central section, providing slidable engagement for the first tongue; ii) a second groove positioned on a second longitudinal side of the central section and extending inward from the second longitudinal side of the central section; the second groove comprising a second gateway, in the second longitudinal side of the central section, providing slidable engagement for the second tongue, wherein the combination of grooves and tongues secure the central section between the first and second endplates; iii) two opposed openings adapted to engage one or more guidewires; iv) a female receptacle adapted to engage a surgical tool; v) an internal chamber; and vi) one or more apertures exposing the internal chamber to the surgically created cavity.

Another preferred embodiment of the current invention can be described as a modular spinal implant adapted for implantation into a surgically created cavity; the modular spinal implant comprising a first anchor positioned at a first site of the surgically created cavity, a second anchor positioned at a second site of the surgically created cavity and a cylindrical-like central section, wherein first and second lengthwise ends of the central section are sandwiched between complementary inward sides of the first anchor and the second anchor anchored to the surgically created cavity: a) the cylindrical-like central section comprising: i) a first interconnector positioned at the first lengthwise end; ii) a second interconnector positioned at the second lengthwise side; b) the first anchor comprising: i) a first inward side coplanar with the first lengthwise end; the first inward side comprising a third interconnector adapted to mate with the first interconnector; ii) a second outward side comprising first grippers adapted to engage the first site, wherein the second outward side of the first anchor is slanted relative to the first inward side; iii) at least two curved edges extending between the first inward side and the second outward side; and iv) first and second slots adapted to receive a surgical instrument distinct from the modular spinal implant allowing the modular spinal implant to be assembled in the surgically created cavity or prior to implantation into the surgically cavity; c) the second anchor comprising: i) a first inward side coplanar with the second lengthwise end, the first inward side comprising a fourth interconnector adapted to mate with the second interconnector; ii) a second outward side comprising second grippers adapted to engage the second site, wherein the second outward side of the second anchor is slanted relative to the first side; iii) at least two curved margins extending between the first inward side and the second outward side; and iv) first and second slots adapted to receive a surgical instrument distinct from the modular spinal implant allowing the modular spinal implant to be assembled in the surgically created cavity or prior to implantation into the surgically cavity.

Still another preferred embodiment of the current invention can be described as a modular spinal implant adapted for implantation into a surgically created cavity; the modular spinal implant comprising a first anchor positioned at a first site of the surgically created cavity, a second anchor positioned at a second site of the surgically created cavity and a cylindrical-like central section, wherein first and second lengthwise ends of the central section are sandwiched between inward sides of the first anchor and the second anchor anchored to the surgically created cavity: a) the cylindrical-like central section comprising: i) a first interconnector positioned at the first lengthwise end; ii) a second interconnector positioned at the second lengthwise side; b) the first anchor comprising: i) a first inward side coplanar with the first lengthwise end; the first inward side comprising a third interconnector adapted to mate with the first interconnector; ii) a second outward side comprising first grippers adapted to engage the first site; and iii) first and second slots adapted to receive a surgical instrument distinct from the modular spinal implant allowing the modular spinal implant to be assembled in the surgically created cavity or prior to implantation into the surgically cavity; c) the second anchor comprising: i) a first inward side coplanar with the second lengthwise end, the first inward side comprising a fourth interconnector adapted to mate with the second interconnector; ii) a second outward side comprising second grippers adapted to engage the second site; and iii) first and second slits adapted to receive a surgical instrument distinct from the modular spinal implant allowing the modular spinal implant to be assembled in the surgically created cavity or prior to implantation into the surgically cavity.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

In the most general sense, the present invention is an implant for bone. The implant can be a modular spinal implant. Among other things, the current invention can be adapted for use with mammalian vertebra. It is believed that the present implant is particularly adapted for implantation into any region of the spine. The current modular spinal implant is adaptable for use with either the state-of-the art anterior entry or posterior entry spinal surgical techniques.

Advantageously, the modular spinal implant can be assembled within the surgical field or surgically created cavity or the spinal implant can also be assembled prior to insertion into the surgically created cavity. Further, embodiments of the modular spinal implant are capable of providing distraction forces and a corridor for insertion of graft and other medically useful substances into the modular spinal implant. It is also anticipated that the corridor or conduit can transport biocompatible devices/substances, such as adhesives, cameras, cannulas, fiber optics, implants, pharmaceuticals, etc.

Preferred embodiments of the present invention are manufactured of titanium alloys, stainless steel, non-resorbable polymers, polyetheretherketone (PEEK) or any other composition acceptable in the art. Embodiments of the current spinal implant can be manufactured of any biocompatible substance or material acceptable in the art or any combination thereof. The present spinal implant can be inserted into the surgical cavity with or without radiography.

Within the scope of the present invention, it has advantageously been discovered apertures of the central section of implant range from about 3 millimeters to about 50 millimeters; widths of the central section range from about 10 millimeters to about 40 millimeters; lengths of the central section range from about 10 millimeters to about 120 millimeters; and depths of the central section range about 10 millimeters to about 28 millimeters. Endplates or anchors of the current invention can have widths of up to about 38 millimeters and heights of up to about 20 millimeters. Endplates can be adapted to provide lordosis for the central section that ranges from about 0 to 20 degrees relative to ground.

Figure 1:
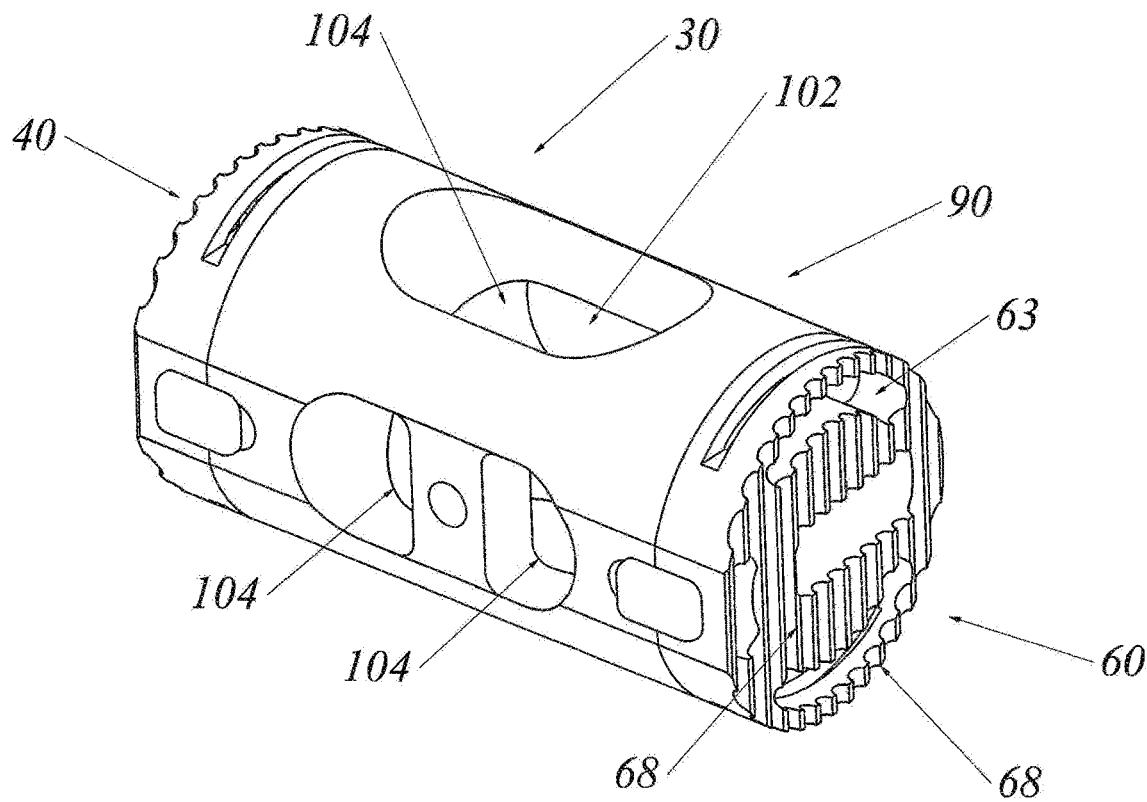
FIG. 1 is a perspective of modular spinal implant (30).
Figure 1A:
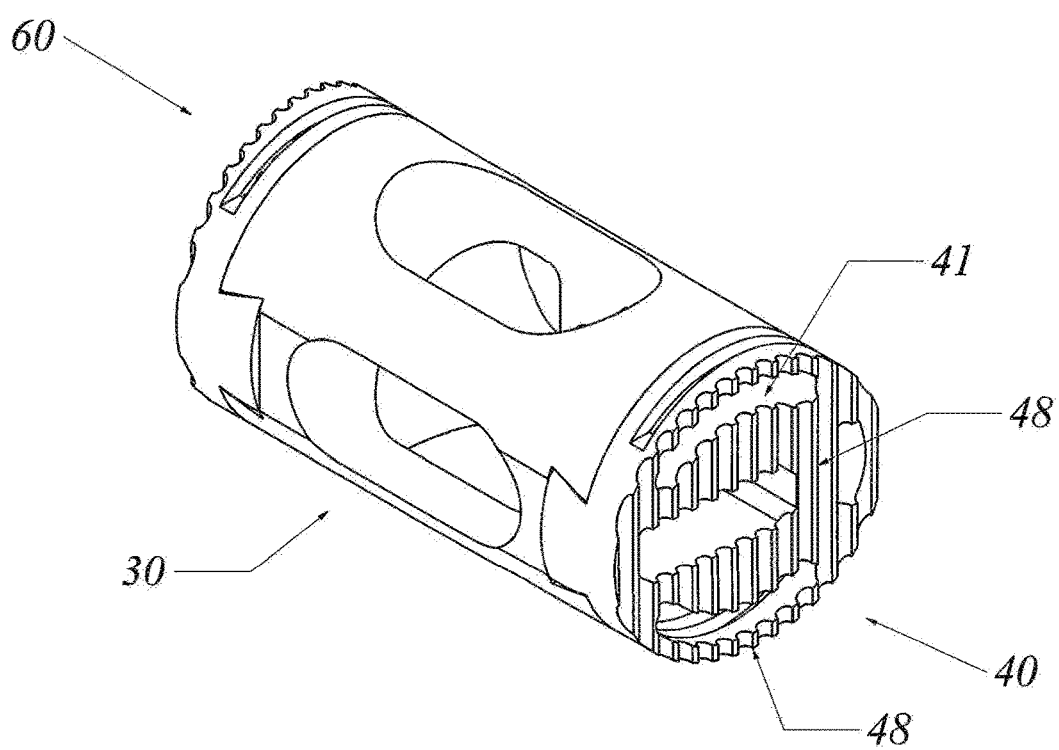
FIG. 1a is frontal view of endplate (40).
Figure 2:
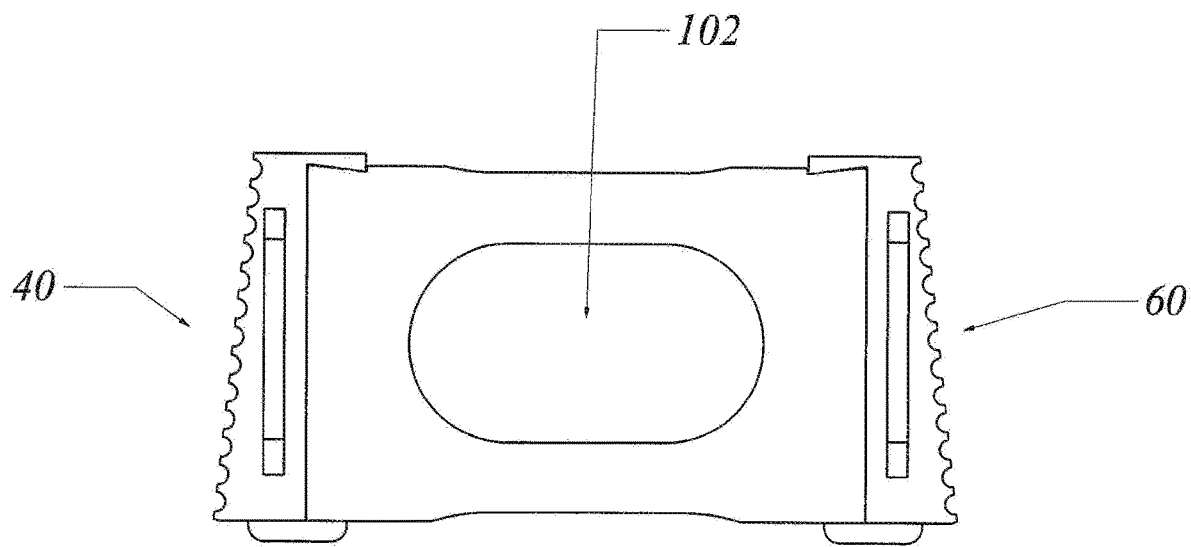
FIG. 2 is a cross-section view of the modular spinal implant (30) shown in FIG. 1.
Figure 3:
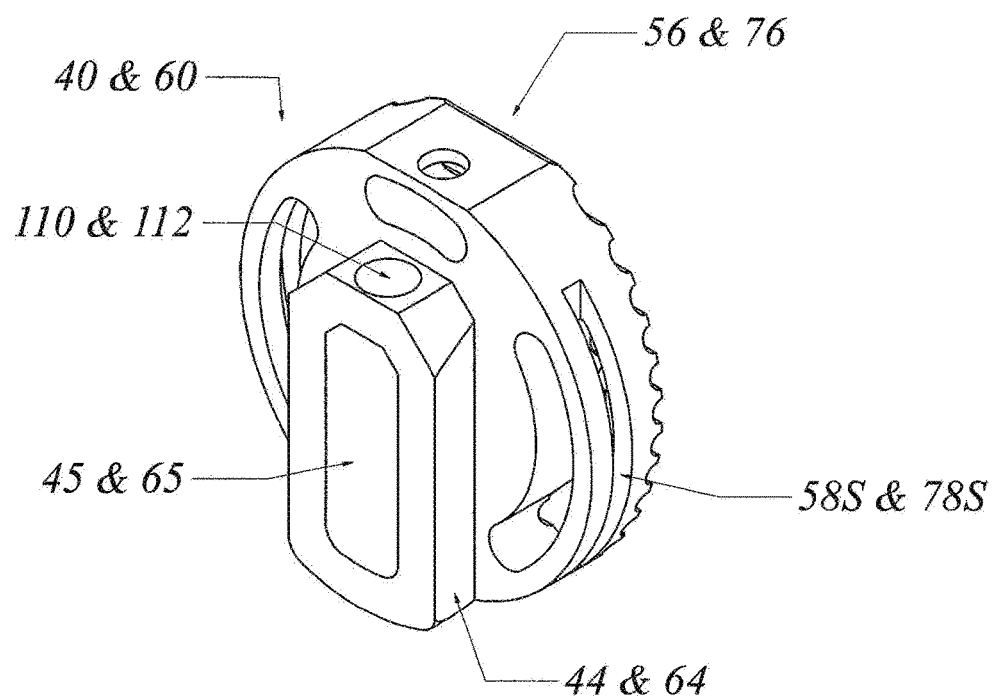
FIG. 3 is a perspective of endplate (40, 60).
Figure 4:
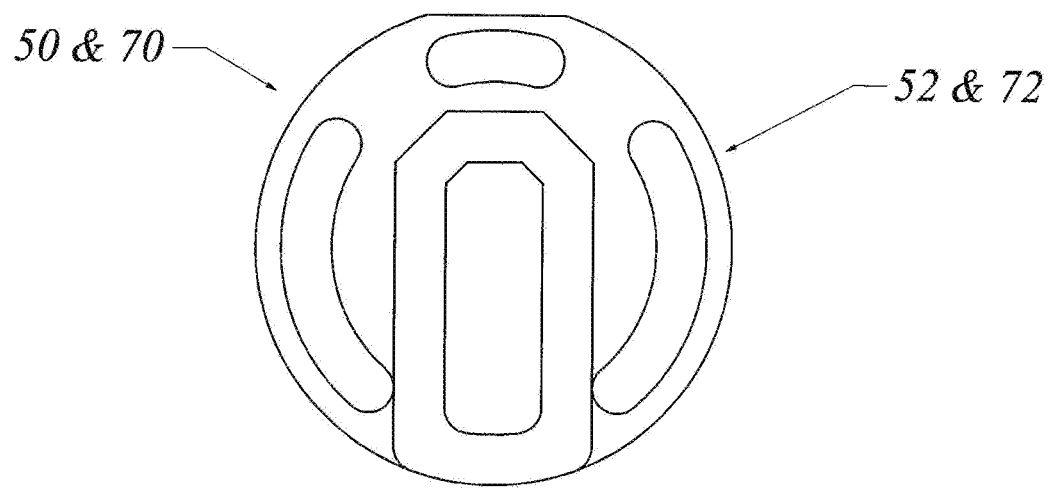
FIG. 4 is a top view of end plate (40, 60) shown in FIG. 3.
Figure 5:
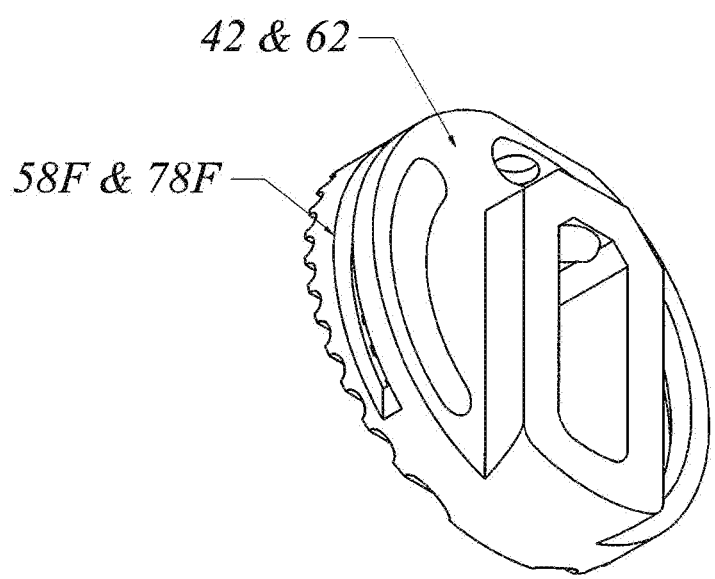
FIG. 5 is another perspective of endplate (40, 60).
Figure 6:
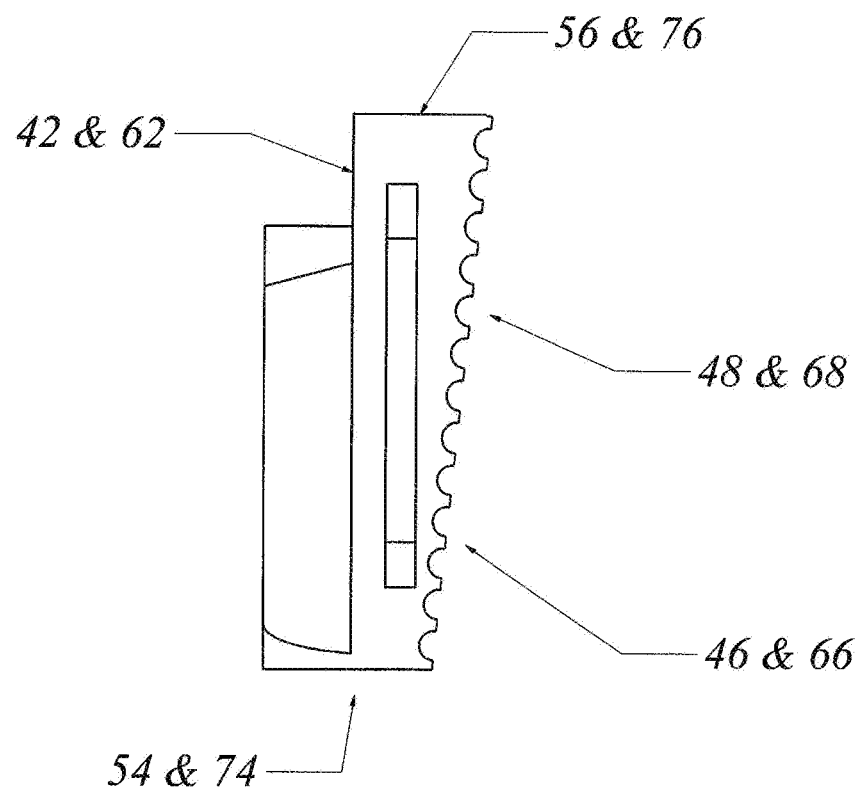
FIG. 6 is side view of endplate (40, 60) shown in FIG. 3.
Figure 7:
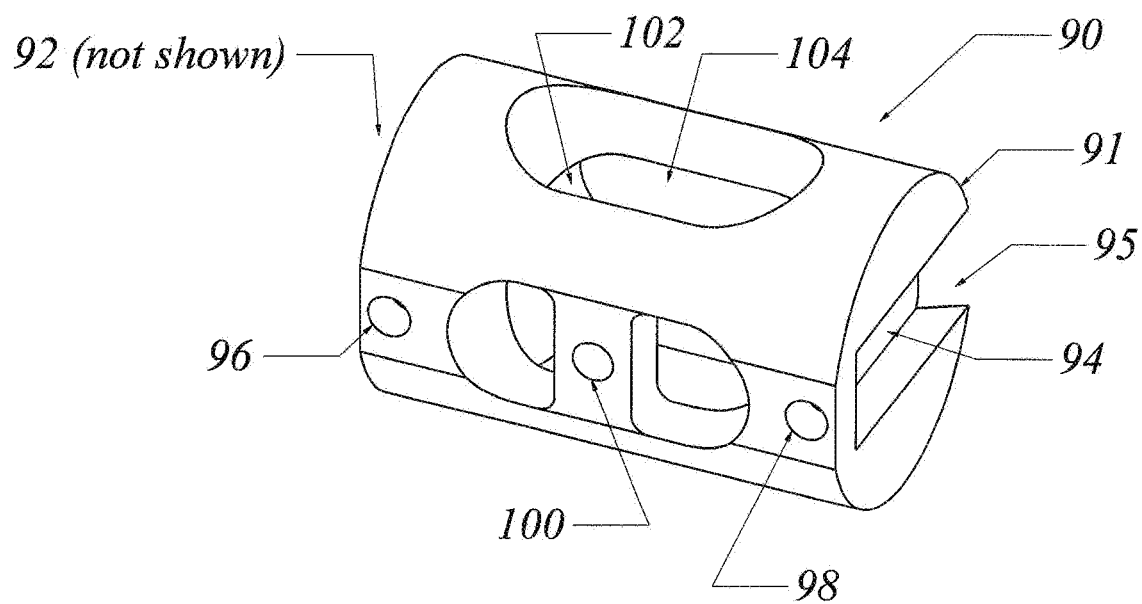
FIG. 7 is a perspective of central section (90).
Figure 8:
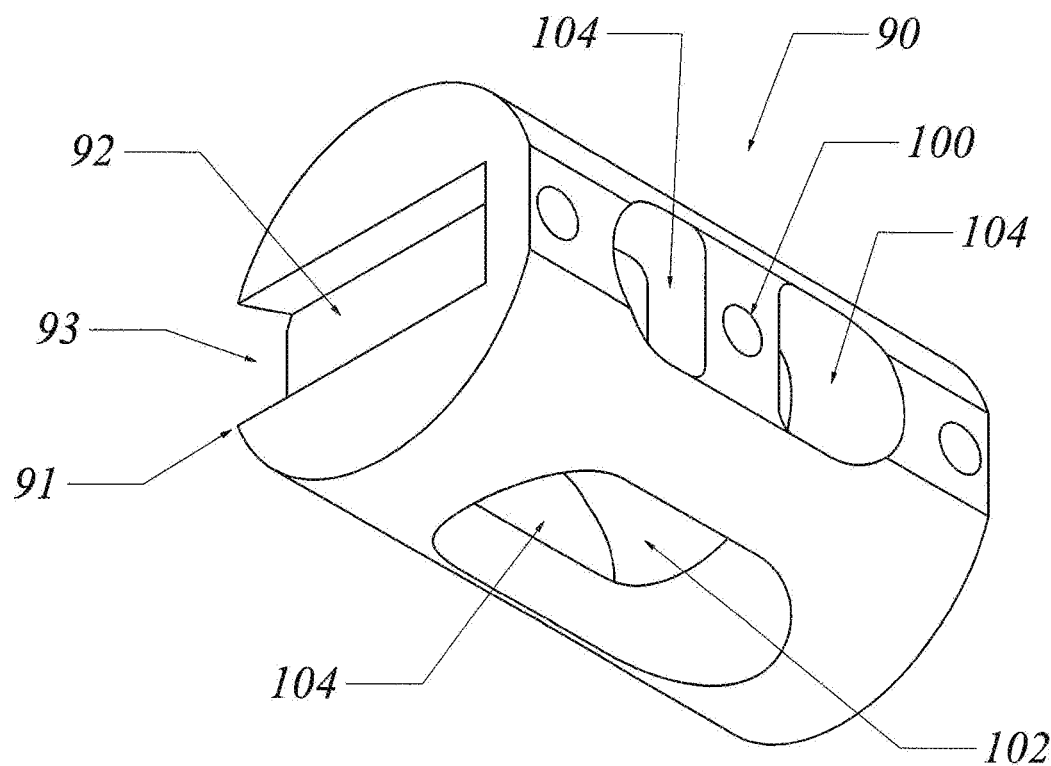
FIG. 8 is another perspective of central section (90).
Figure 9:
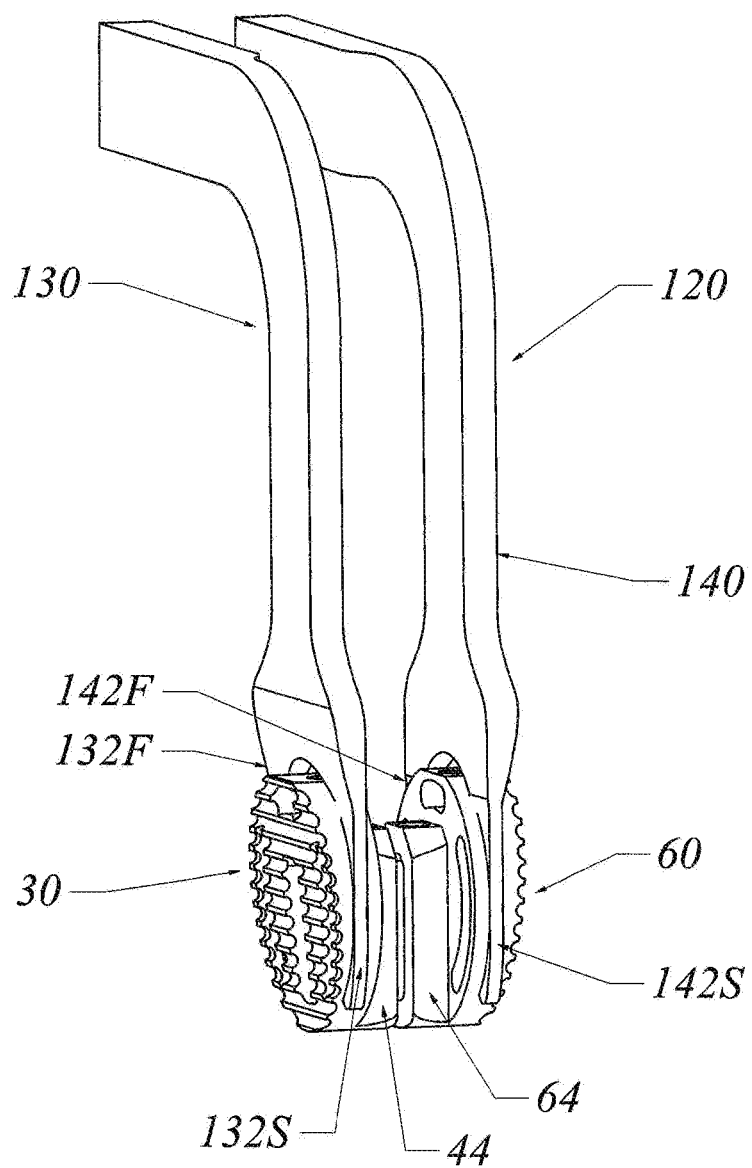
FIG. 9 is a perspective of insertion tool component (120).
Figure 10:
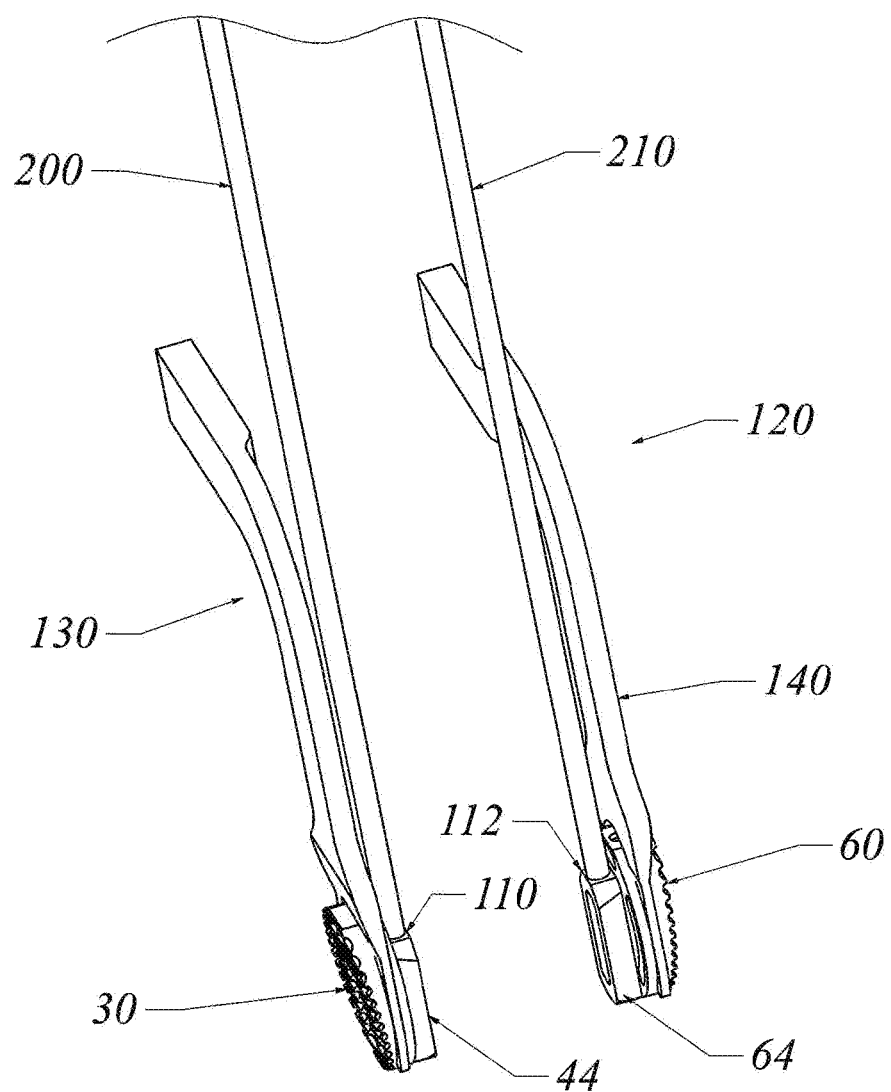
FIG. 10 is a perspective of insertion tool component (120).
Figure 11:
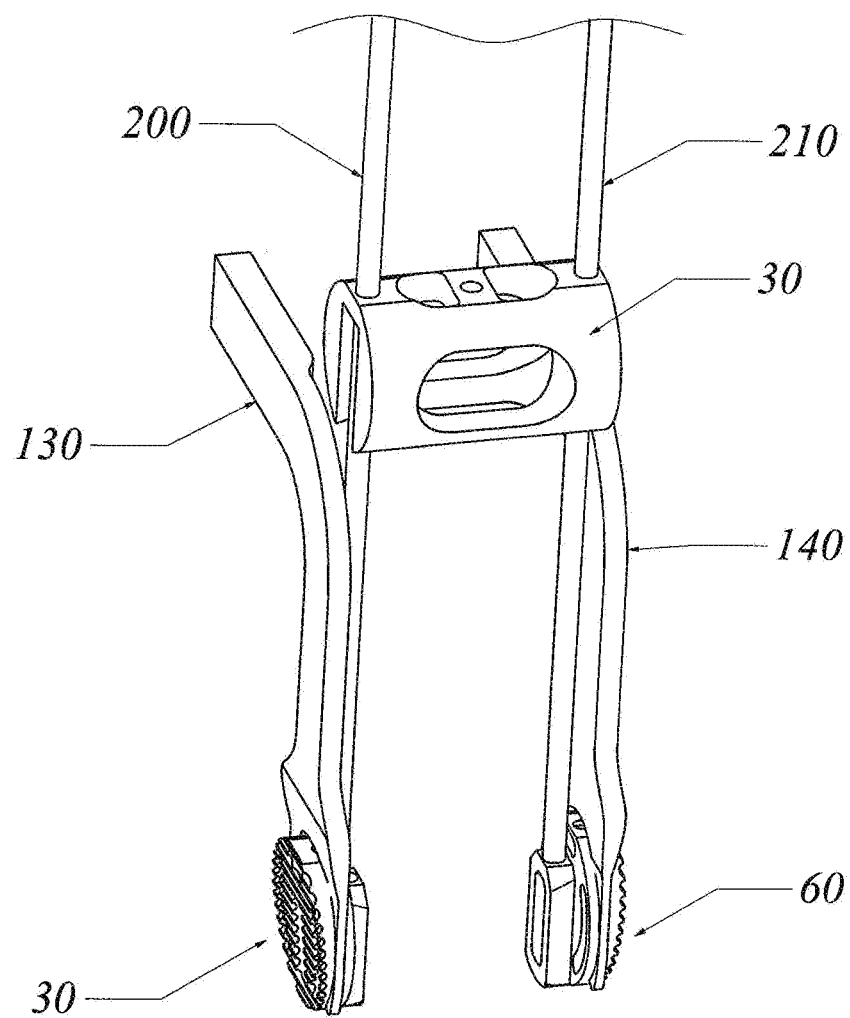
FIG. 11 is perspective of insertion tool component (120) and modular spinal implant (30).

Enabled preferred embodiments of spinal implant component (30) and insertion tool component (120) are portrayed in FIGS. 1-11. In some of the Figures, for similar parts of spinal implant's (30) first endplate or anchor (40) and second endplate or anchor (60), different reference numbers identify similar elements associated with both the first anchor (40) and the second anchor (60). Those skilled in the art recognize that spinal implant (30) can be used in numerous surgeries in different regions of the body. Because of this fact, the potential kinds of surgically created cavities into which spinal implant (30) can be implanted or inserted are not shown in the Drawings.

The spinal implant or spinal implant component (30) adapted for implantation into a surgically created cavity is provided with a first endplate (40) positioned at a first site of the surgically created cavity, a second endplate (60) positioned at a second site opposed from the first site of the surgically created cavity and a central section (90) positioned between the opposed endplates (40, 60).

First endplate (40) has a first planar side (42) that includes a first tongue or interconnector (44) perpendicular to the first planar side (42) and extending toward the center of the spinal implant (30) and a second side (46) opposed to the first planar side (42) where the second side (46) has grippers (48) adapted to engage the first site. First endplate (40) can be provided with first orifice (41) extending through the first endplate (42). In select embodiments of first endplate (40), a first portion of grippers (48) encircles the first orifice (41) and a second portion of the grippers (48) spans across the first orifice (41). First endplate (40) is also provided with opposed first and second curved edges (50, 52) positioned between opposed first and second linear edges (54, 56) where the edges (50, 52, 54, 56) extend between the first planar side (42) and the second side (46). As shown, the first linear edge (54) is of lesser length than the second linear edge (56) creating an angled second side (46) relative to the first planar side (42). Slots (58F, 58S) traverse the approximate length of each curved edge (50, 52). Select preferred embodiments of first tongue (44) can include a channel (110) adapted to receive a first guidewire (200). Interlocker (44) can include a gap (45) extending outward from the first orifice (41).

Second endplate (60) has a first planar side (62) that includes a second tongue or interlocker (64) perpendicular to the first planar side (62) and extending toward the first tongue or interlocker (44) and a second side (66) opposed to the first planar side (62) where the second side (66) has grippers (68) adapted to engage the second site. Second endplate (60) can be provided with second orifice (63) extending through the second endplate (60). In select embodiments of second endplate (40), a first portion of grippers (68) encircles the second orifice (63) and a second portion of the grippers (68) spans across the second orifice (63). Second endplate (60) is also provided with opposed first and second curved margins (70, 72) positioned between opposed first and second linear margins (74, 76) where the margins (70, 72, 74, 76) extend between the first planar side (62) and the second side (66). As shown, the first margin (74) is of lesser length than the second linear margin (76) creating an angled second side relative to the first planar side (62). Slits (78F, 78S) traverse the approximate length of each curved margin (70, 72). Select preferred embodiments of second tongue (64) can include a conduit (112) adapted to receive a second guidewire (210). Interlocker (64) can include a gap (65) extending outward from the second orifice (63).

Spinal implant (30) is also provided with a central section (90) connected to the first endplate (40) and the second endplate (60). In select preferred embodiments of the current invention, central section (90) is sandwiched between first anchor (40) and second anchor (60) anchored to the surgically created cavity. Central section (90) has a first groove or interlocker (92) for engaging the first tongue or interlocker (44) and a second groove or interlocker (94) for engaging the second tongue or interlocker (64). The combination of grooves and tongues or interlockers (92, 94, 44, 64) secure the central section (90) between the first and second endplates (40, 60). Interlocker (92) can include first gateway (93) in wall (91) and interlocker (94) can include second gateway (95) in wall (91) of interlocker (94) providing engagement with interlockers (44, 64). Regardless of the design of interlockers (92, 94, 44, 64) utilized, each interlocker adapted to mate with its corresponding interlocker. In select preferred embodiments, one or more detents (not shown) can be included to further secure the combination of grooves and tongues (92, 94, 44, 64). Central section (90) can also be provided with: two opposed openings (96, 98) adapted to engage one or more guidewires (200, 210); a female receptacle (100) adapted to engage a surgical tool (not shown); an internal chamber (102); and one or more apertures (104) exposing the internal chamber (102) to the surgically created cavity (not shown).

Preferred embodiments of the insertion tool component (120) can be provided with: a detachable first handle (130) with two prongs (132F, 132S) for engaging the first and second slots (58F, 58S) of first endplate (40) and a detachable second handle (140) with two tines (142F, 142S) for engaging the first and second slits (78F, 78S) of second endplate (60). It was discovered that combination of first handle (130) and first endplate (40) and second handle (140) and second endplate (60) can create a distraction device for improving ease of insertion of central section (90) onto tongues (44, 64) of endplates or anchors (40, 60) attached to the surgically created cavity. Although not shown in the Drawings, it has been discovered that prongs (132F, 132S) can be provided with first and second caliper components to measure one or more spaces of the surgically created cavity.

In accordance with the present invention, when surgical parameters require, tongues (44, 64) can be positioned on central section (90) and grooves (92, 94) positioned on endplates or anchors (40, 60). Within the scope of the current invention, anchors (40, 60) can be structures other than plate-like endplates.

Another preferred embodiment of modular spinal implant (30) is provided with a first anchor (40) positioned at a first site of the surgically created cavity, a second anchor (60) positioned at a second site opposed from the first site of the surgically created cavity and a central section (90) positioned between opposed anchors (40, 60).

First anchor (40) has a first smooth side (42) that includes a first tongue (44) extending toward the center of the spinal implant (30) and a second side (46) opposed to the first planar side (42) where the second side (46) has grippers (48) adapted to engage the first site. First anchor (40) is also provided with opposed first and second curved edges (50, 52) positioned between opposed first and second linear edges (54, 56) where the edges (50, 52, 54, 56) extend between the first smooth side (42) and the second side (46). Slots (58F, 58S) traverse the approximate length of each curved edge (50, 52). Select preferred embodiments of first tongue (44) can include a channel (110) adapted to receive a first guidewire (200).

Second anchor (60) has a first smooth side (62) that includes a second tongue (64) extending toward the first tongue (44) and a second side (66) opposed to the first smooth side (62) where the second side (66) has grippers (68) adapted to engage the second site. Second anchor (60) is also provided with opposed first and second curved margins (70, 72) positioned between opposed first and second linear margins (74, 76) where the margins (70, 72, 74, 76) extend between the first planar side (62) and the second side (66). Slots (78F, 78S) traverse the approximate length of each curved margin (70, 72). Select preferred embodiments of second tongue (64) can include a conduit (112) adapted to receive a second guidewire (210).

Applicant has enabled, described and disclosed the invention as required by Title 35 of the United States Code.

What is claimed is:

1. A modular spinal implant adapted for implantation into a surgically created cavity; the modular spinal implant comprising:
   a) an annular central section comprising a first longitudinal end groove and an opposed second longitudinal end groove;
   b) a first tongue, extending from a first inward side of a first anchor, configured to interlock with the first longitudinal end groove connecting the first anchor to the annular central section and a second outward side of the first anchor comprising first grippers adapted to engage first site of the surgically created cavity; and
   c) a second tongue, extending from an inner side of a second anchor, configured to interlock with the second longitudinal end groove connecting the second anchor to the annular central section and a second outer side of the second anchor comprising second grippers adapted to engage the a second site of the surgically created cavity, wherein the modular spinal implant is assembled in the surgically created cavity or prior to implantation into the surgically created cavity.

2. The modular spinal implant of claim 1, wherein:
   a) the first anchor comprises at least one or more curved edges extending between the first inward side of the first anchor and the second outward side of the first anchor; and
   b) the second anchor comprises one or more curved margins extending between the first inner side of the second anchor and the second outer side of the second anchor.

3. The modular spinal implant of claim 1, wherein
   a) the first anchor comprises first and second slots adapted to receive a surgical instrument distinct from the modular spinal implant and
   b) the second anchor comprises first and second slits adapted to receive a surgical instrument distinct from the modular spinal implant.

4. The modular spinal implant of claim 3 further comprising a device distinct from the modular spinal implant for inserting the modular spinal implant into the surgically created cavity, wherein the device comprises:
   a) a first handle comprising two prongs adapted to engage the first and second slots of the first anchor; and
   b) a second handle comprising two tines adapted to engage the first and second slits of the second anchor.

5. The modular spinal implant of claim 1 comprising:
   a) an internal chamber; and
   b) one or more apertures exposing the internal chamber to the surgically created cavity.

6. The modular spinal implant of claim 1, wherein:
   a) the first anchor comprises a first orifice extending through the first anchor;
   b) the second anchor comprises a second orifice extending through the second anchor; and
   c) a first portion of the first and second grippers encircles the first and second orifices and a second portion of the first and second grippers spans across the first and second orifices.

7. A modular spinal implant adapted for implantation into a surgically created cavity; the modular spinal implant comprising:
   a) an annular central section comprising a first longitudinal end groove and an opposed second longitudinal end groove;
   b) a first anchor comprising: a first tongue, extending from a first inward side of the first anchor connected to the first longitudinal end groove the first end interlocker and a second outward side comprising first grippers; and
   c) a second anchor comprising: a second tongue, extending from a first inner side of the second anchor connected to the second longitudinal end groove and a second outer side comprising second grippers, wherein after the spinal implant is assembled, the annular central section, the first anchor and the second anchor have consistent diameters with respect to each other.

8. The modular spinal implant of claim 7, wherein:
   a) the first anchor comprises at least one or more curved edges extending between the first inward side of the first anchor and the second outward side of the first anchor; and
   b) the second anchor comprises one or more curved margins extending between the first inner side of the second anchor and the second outer side of the second anchor.

9. The modular spinal implant of claim 7, wherein
   a) the first anchor comprises first and second slots adapted to receive a surgical instrument distinct from the modular spinal implant; and
   b) the second anchor comprises first and second slits adapted to receive a surgical instrument distinct from the modular spinal implant.

10. The modular spinal implant of claim 9 further comprising a device distinct from the modular spinal implant for inserting the modular spinal implant into the surgically created cavity, wherein the device comprises:
   a) a first handle comprising two prongs adapted to engage the first and second slots of the first anchor; and
   b) a second handle comprising two tines adapted to engage the first and second slits of the second anchor.

11. The modular spinal implant of claim 7 comprising:
   a) an internal chamber; and
   b) one or more apertures exposing the internal chamber to the surgically created cavity.

12. The modular spinal implant of claim 7, wherein:
   a) the first anchor comprises a first orifice extending through the first anchor;
   b) the second anchor comprises a second orifice extending through the second anchor; and
   c) a first portion of the first and second grippers encircles the first and second orifices and a second portion of the first and second grippers spans across the first and second orifices.

13. An anchor for securing a first side of a central section of a modular spinal implant to a first site of a surgically created cavity; the anchor comprising:
   a) an inward side tongue of the anchor engaging a longitudinal end groove of the central section of the modular spinal implant;
   b) a second outward side comprising grippers adapted to engage the first site; and
   c) curved edges extending between the inward side and the second outward side of the anchor, wherein after the anchor is connected with the central section of the modular spinal implant, diameters of the anchor and the central section are consistent with each other.

14. The anchor of claim 13 comprising first and second slots adapted to receive a surgical instrument distinct from the modular spinal implant.

15. The anchor of claim 14 comprising an orifice extending through the anchor.

16. The anchor of claim 15, wherein a first portion of the grippers encircles the orifice and a second portion of the grippers spans across first the orifice.

17. The anchor of claim 16, wherein first and second slots traverse an approximate length of each curved edge.

18. The anchor of claim 13, wherein the tongue is lesser length than the inward side of anchor.

* * * * *